United States Patent
Kobayashi

(10) Patent No.: US 9,782,603 B2
(45) Date of Patent: Oct. 10, 2017

(54) LIVING BODY STIMULATOR

(71) Applicant: TECHNO LINK CO., LTD., Niigata-shi, Niigata (JP)

(72) Inventor: Tatsuyuki Kobayashi, Niigata (JP)

(73) Assignee: TECHNO LINK CO., LTD., Niigata-Shi, Niigata (JP)

( * ) Notice: Subject to any disclaimer, the term of this patent is extended or adjusted under 35 U.S.C. 154(b) by 282 days.

(21) Appl. No.: 14/552,604

(22) Filed: Nov. 25, 2014

(65) Prior Publication Data
US 2016/0096033 A1    Apr. 7, 2016

(30) Foreign Application Priority Data

Oct. 2, 2014   (JP) ................................ 2014-203947

(51) Int. Cl.
*A61N 5/06*     (2006.01)
*A61B 18/00*    (2006.01)

(52) U.S. Cl.
CPC ............. *A61N 5/06* (2013.01); *A61N 5/0616* (2013.01); *A61B 2018/00708* (2013.01);
(Continued)

(58) Field of Classification Search
CPC ................................ A61N 5/06; A61N 5/0616
(Continued)

(56) References Cited

U.S. PATENT DOCUMENTS 6,273,884 B1 *   8/2001   Altshuler ............. A61B 18/203
                                                            606/2
6,290,713 B1 *   9/2001   Russell ................. A61N 5/0616
                                                            607/88
(Continued)

FOREIGN PATENT DOCUMENTS

EP          2462985 A1     6/2012
JP         10-028714 A     2/1998
(Continued)

OTHER PUBLICATIONS

EP Search Report mailed in corresponding EP Application No. 14003822 on Jan. 29, 2016.
(Continued)

*Primary Examiner* — John R Downey
(74) *Attorney, Agent, or Firm* — Fox Rothschild LLP

(57) ABSTRACT

Provided is a living body stimulator capable of bringing about a stable treatment effect through a light stimulation without increasing the temperature of an irradiation surface more than necessary. This invention is a living body stimulator for stimulating a living body through a light irradiation from a light source. This stimulator includes a temperature sensor for detecting the temperature of the irradiation surface in contact with the living body; and a brightness control unit for changing and controlling the brightness of the light source such that the temperature of the irradiation surface becomes not higher than 42° C., by receiving a detection output from the temperature sensor. The brightness control unit is capable of extending a period of irradiation from the light source in accordance with a decrease in the brightness thereof, when decreasing such brightness through a control regulation.

13 Claims, 5 Drawing Sheets

(52) U.S. Cl.
CPC ............... *A61B 2018/00791* (2013.01); *A61N 2005/0626* (2013.01); *A61N 2005/0627* (2013.01)

(58) Field of Classification Search
USPC .......................................... 606/2, 9; 607/88
See application file for complete search history.

(56) References Cited

U.S. PATENT DOCUMENTS

| | | | | |
|---|---|---|---|---|
| 6,451,007 | B1* | 9/2002 | Koop | A61B 18/20 128/898 |
| 6,682,524 | B1* | 1/2004 | Elbrecht | A61B 18/203 606/13 |
| 2003/0100936 | A1* | 5/2003 | Altshuler | A61F 7/02 607/96 |
| 2005/0222648 | A1* | 10/2005 | Simonsen | A61B 18/203 607/86 |
| 2006/0282134 | A1* | 12/2006 | Shapiro | A61F 7/007 607/88 |
| 2006/0287696 | A1* | 12/2006 | Wright | A61N 5/0613 607/88 |
| 2009/0133691 | A1* | 5/2009 | Yamada | A61M 11/041 128/200.16 |
| 2010/0211136 | A1 | 8/2010 | De Taboada et al. | |
| 2011/0034971 | A1* | 2/2011 | Svanberg | A61N 5/0601 607/88 |
| 2011/0144410 | A1* | 6/2011 | Kennedy | A61K 31/327 600/2 |
| 2012/0143291 | A1* | 6/2012 | Owens | A61B 18/203 607/90 |
| 2013/0066403 | A1* | 3/2013 | Giraud | A61B 18/203 607/89 |

FOREIGN PATENT DOCUMENTS

| | | |
|---|---|---|
| JP | 4084903 B | 4/2008 |
| JP | 2012095803 | 5/2012 |
| JP | 2012-165906 A | 9/2012 |
| JP | 2013146528 | 8/2013 |
| JP | 2014-000406 A | 1/2014 |
| WO | 2007/090256 A1 | 8/2007 |
| WO | 2009104854 A2 | 8/2009 |
| WO | 2010/078581 A1 | 7/2010 |

OTHER PUBLICATIONS

Office Action dated Aug. 1, 2017 issued in the corresponding Japanese patent application No. 2014-203947.

* cited by examiner

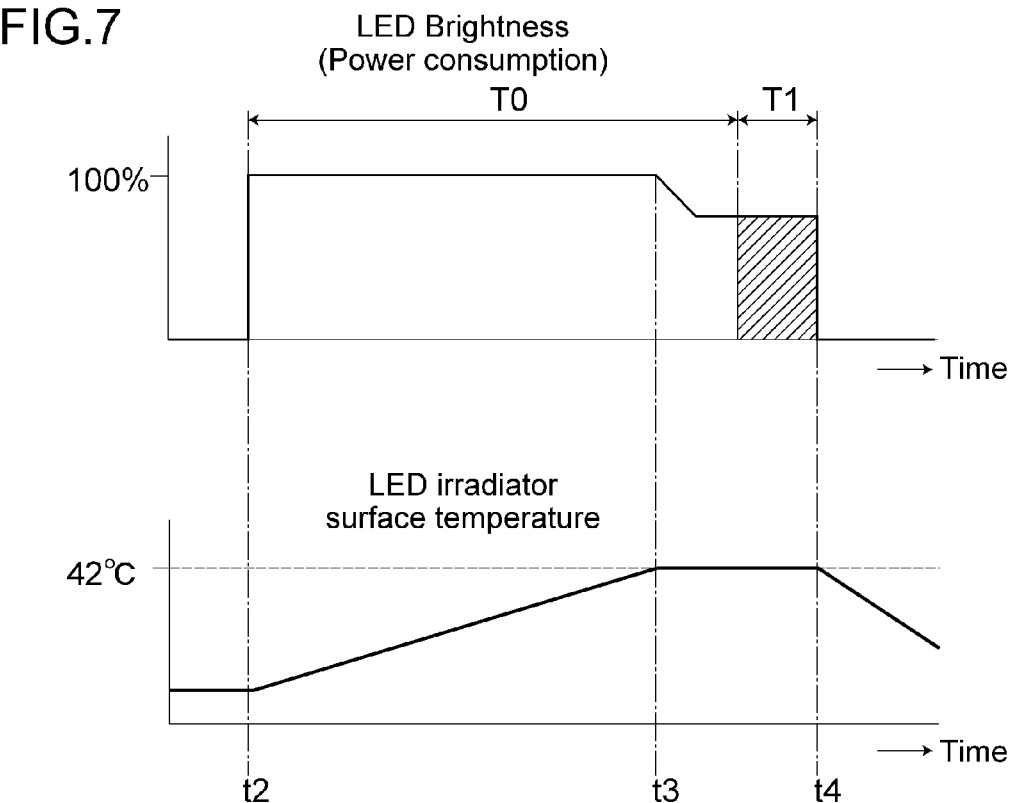
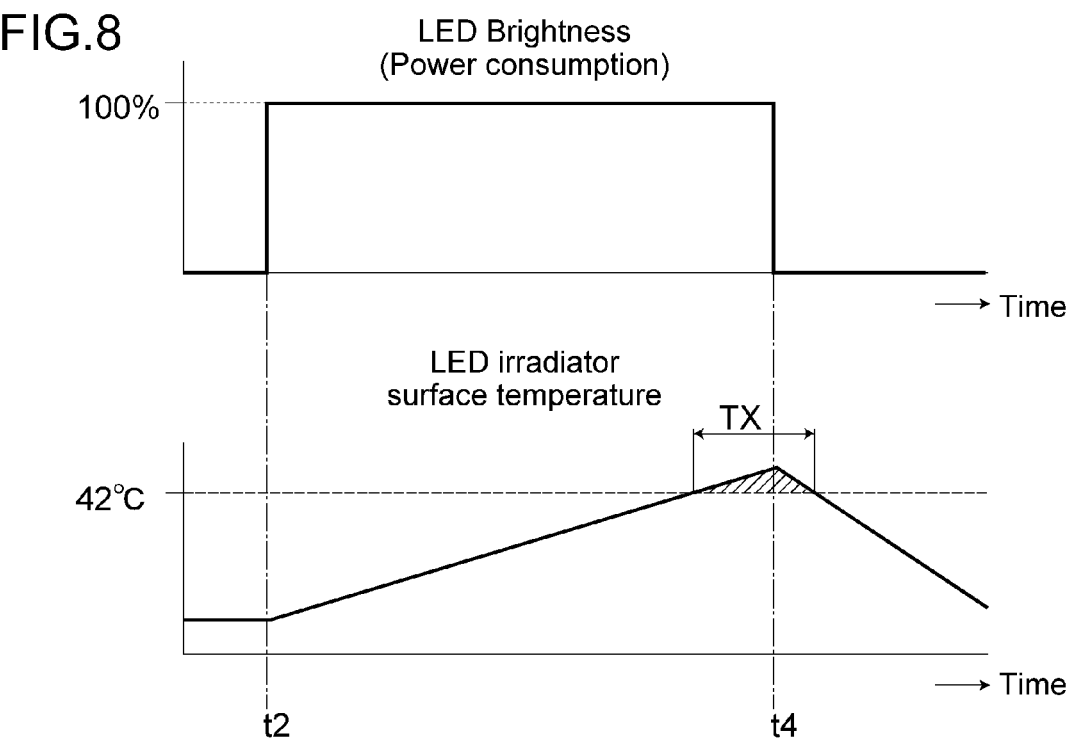

LIVING BODY STIMULATOR

CROSS REFERENCE TO RELATED APPLICATIONS

This US Application claims priority to Japanese Application No.: 2014-203947 filed Oct. 2, 2014, entitled "LIVING BODY STIMULATOR" the entirety of which is incorporated herein by reference.

BACKGROUND OF THE INVENTION

Field of the Invention

The present invention relates to a living body stimulator capable of bringing about positive effects by irradiating lights from a light source to the living body; the effects vary corresponding to the wavelengths of the light.

Description of Related Art

As it has been verified in many articles, irradiating a human body with lights of various wavelengths brings about positive effects corresponding to such wavelengths. In this way, in the cosmetic and medical field, there have been developed a number of treatment devices for various purposes, as living body stimulators utilizing light stimulation.

For example, disclosed in JP-A-2013-146528 is a treatment device for stimulating a patient's fibroblast by irradiating a red or yellow light from an LED (light emitting diode). Further, disclosed in JP-A-2012-95803 is an idea of irradiating a living tissue with a stimulus light(s) of one or two kinds of wavelengths.

SUMMARY OF THE INVENTION

With regard to the aforementioned prior arts, there had not been much of a problem for a low-power device concerning a light source self-heating as long as a conventional small LED is used as a light source in the device. However, in recent years, high-power LEDs have been used to improve an efficiency and thereby increase a light output. For this reason, a significant increase in the power consumption of the heat-generating light source is expected to cause a temperature affecting a living body to rise more than necessary, thereby requiring the living body to be protected in such case.

Yet another problem is as follows. That is, the temperature of an irradiation surface is nearly identical to the ambient temperature when starting using the device. Here, since the device is used by inevitably allowing the irradiation surface to be directly in contact with the bare skin, a sudden cold feeling that occurs at the time of contact has made the user uncomfortable.

The present invention has been made to solve the aforementioned problems. Particularly, a first object of the invention is to provide a living body stimulator capable of achieving a stable treatment effect through a light stimulation, without increasing the temperature of the irradiation surface more than necessary.

Moreover, a second object of the invention is to provide a living body stimulator capable of resolving the uncomfortable feeling that occurs when the living body has come into contact with the irradiation surface.

The invention of a first aspect is a living body stimulator for stimulating a living body through a light irradiation from a light source, including: a temperature detection unit for detecting a temperature of an irradiation surface in contact with the living body; and a brightness control unit for changing and controlling a brightness of the light source such that the temperature of the irradiation surface becomes not higher than 42° C., by receiving a detection output from the temperature detection unit. Here, the brightness control unit also serves to extend an irradiation period in accordance with a decrease in the brightness of the light source when the control unit has been regulated to decrease the brightness of the light source.

The invention of a second aspect further includes: one or more light irradiators for irradiating lights from the light source through the irradiation surface; and an operation device electrically connected to the light irradiators in a wired or wireless manner, the operation device including a temperature monitoring control unit capable of constantly monitoring the temperature of the irradiation surface and outputting a monitoring result, by receiving the detection output from the temperature detection unit.

The invention of a third aspect further includes a preheating control unit allowing the irradiation surface to be controllably preheated, before the living body is stimulated by the light irradiation from the light source.

According to the invention of the fourth aspect, the brightness control unit is configured to enable a setting of a first mode achieving a constant irradiation power consumption of the light source, the first mode extending the irradiation period of the light source in accordance with a decrease in brightness of the light source when the brightness of the light source has been decreased through control; and a setting of a second mode achieving a constant irradiation period of the light source, the second mode allowing a light irradiation from the light source to end in a preset irradiation period while controlling the temperature of the irradiation surface to not higher than 42° C.

The invention of the fifth aspect comprises an irradiation period setting tool for changing and setting the irradiation period in the second mode.

The invention of the sixth aspect comprises a plurality of light irradiators individually irradiating a light from the light source through the irradiation surface, wherein the brightness control unit, in the first mode, uses one of the light irradiators whose irradiation surface temperature has first reached 42° C. as a reference to match irradiation ending times of the rest of the light irradiators to an irradiation ending time of the light irradiator used as the reference.

According to the invention of the seventh aspect, the temperature monitoring control unit, after determining that the temperature of the irradiation surface of a particular light irradiator has become abnormal, serves to stop power supply to the particular light irradiator and send out an alarm signal, while maintaining a communication between the particular light irradiator and the operation device and keeping monitoring the temperature of the irradiation surface.

The invention according to the eighth aspect comprises a preheating unit for preheating the irradiation surface, wherein the preheating control unit enables a setting of a first mode in which, during a period between when preheating is started and when a preheating period elapses, power supply to the preheating unit is stopped to end preheating the irradiation surface when the temperature of the irradiation surface that is obtained through the detection output from the temperature detection unit has increased to a first temperature; or when the preheating period has elapsed if the temperature of the irradiation surface has not increased to the first temperature.

The invention according to the ninth aspect comprises a preheating period setting unit for changing and setting a preheating period of the irradiation surface.

According to the invention of the tenth aspect, the preheating control unit is configured to enable a setting of a second mode other than the first mode, the second mode allowing an electric conduction of the preheating unit to be turned off when the temperature of the irradiation surface has increased to a second temperature, but the electric conduction of the preheating unit to be turned on when the temperature of the irradiation surface has decreased to a third temperature.

According to the invention of the first aspect, the brightness control unit serves to automatically control the brightness of the light source such that the temperature of the irradiation surface in contact with the living body does not exceed 42° C. which is lower than 44° C. as the temperature causing low temperature burn. In addition, when the brightness of the light source has been decreased through the control regulation, the time of irradiation from the light source to the living body will be automatically extended such that the brightness decreased will be compensated, thus preventing the treatment effects from varying. Therefore, there can be achieved a stable treatment effect of the light stimulus from the light source, without increasing the temperature of the irradiation surface more than necessary.

According to the invention of the second aspect, on the side of the operation device that is electrically connected to the light irradiator(s), outputted from the temperature monitoring control unit is the result obtained by constantly monitoring the temperature of each irradiation surface during the use of the device, such result being signaled to the user in the form of a display or a sound. Thus, even when the temperature of each irradiation surface cannot be properly controlled due to a malfunction or failure of the device, the user is capable of recognizing the abnormal heat generation through the output of the temperature monitoring control unit.

According to the invention of the third aspect, the irradiation surface is heated in advance to a temperature inducing no cold feeling, before irradiating the living body with light. Therefore, there can be resolved the uncomfortable feeling that occurs at the time of allowing the bare skin of the living body to come into contact with the irradiation surface.

According to the invention of the fourth aspect, the brightness control unit enables not only the setting of the first mode, but also the setting of the second setting. Therefore, while both the first and second modes allow the living body in contact with the irradiation surface to be protected during treatment, the second mode can be selected to avoid the patient's dislike for the prolonged treatment period when only the first mode is available.

According to the invention of the fifth aspect, by operating the irradiation period setting tool, the user can have his/her living body irradiated with light for a preferred and preset treatment period, with the second mode being set.

According to the invention of the sixth aspect, even when the light irradiators may vary from one another, all the light irradiators can be configured to end irradiation form the light source at an identical time.

According to the invention of the seventh aspect, the user is allowed to recognize the abnormal state of the device; and the electric current supply to the light irradiator in the abnormal state can be stopped immediately, thus improving a safety.

According to the invention of the eighth aspect, the first mode stops power supply to the light source and the heat generating unit when the irradiation surface has reached the desired first temperature. For this reason, the power consumption can be prevented from being wasted. Further, even when the temperature rise of the irradiation surface is slow due to a surrounding environment, by continuously preheating the irradiation surface before the preheating period elapses, there can be resolved as much as possible the uncomfortable feeling felt by the patient when the bare skin of his/her living body has come into contact with the irradiation surface.

According to the invention of the ninth aspect, by operating the preheating period setting unit, the user is allowed to preheat the irradiation surface for a preferred and preset preheating period.

According to the invention of the tenth aspect, the second mode allows the irradiation surface to be preheated again in a repetitive manner in accordance with the change in the irradiation surface temperature. Therefore, even when the period between when the power switch is operated and when the bare skin of the living body comes into contact with the irradiation surface becomes long, the temperature of the irradiation surface can be maintained close to the body temperature, thus making it possible to reliably resolve the uncomfortable feeling felt by the patient when the bare skin of his/her living body has come into contact with the irradiation surface.

BRIEF DESCRIPTION OF THE DRAWINGS

FIG. 7 is a graph showing changes in the LED brightness and the irradiation surface temperature with time in the aforementioned embodiment.

FIG. 8 is a graph showing changes in the LED brightness and the irradiation surface temperature with time, when using a conventional device.

DETAILED DESCRIPTION OF THE INVENTION

A preferred embodiment of a living body stimulator of the present invention is described hereunder with reference to the accompanying drawings.

Figure 1:
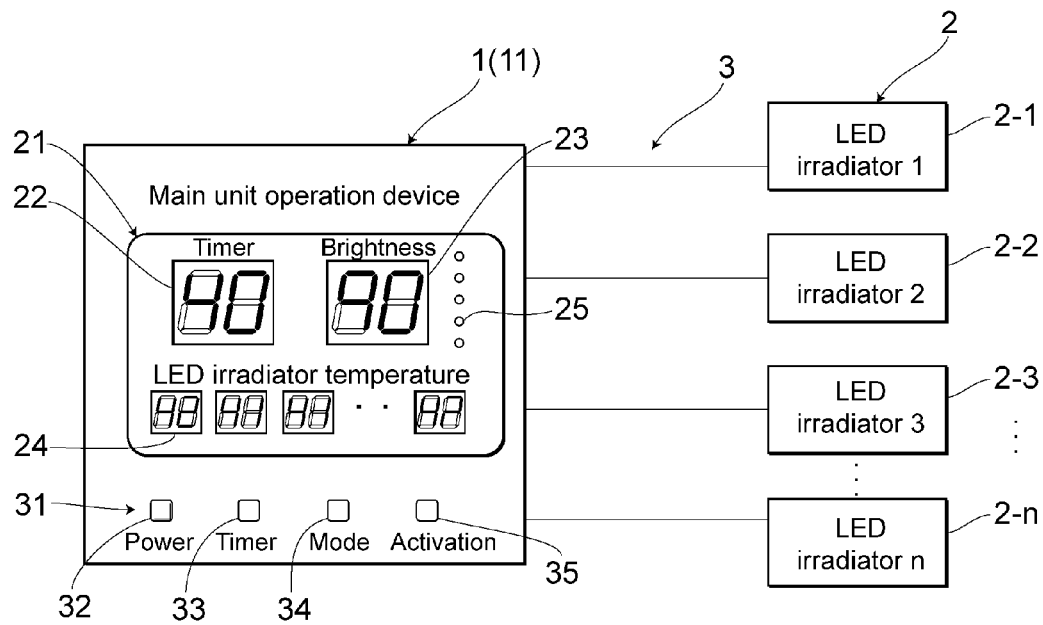
FIG. 1 is a diagram showing an exterior structure of a wired living body stimulator of a preferred embodiment of the present invention.
Figure 2:
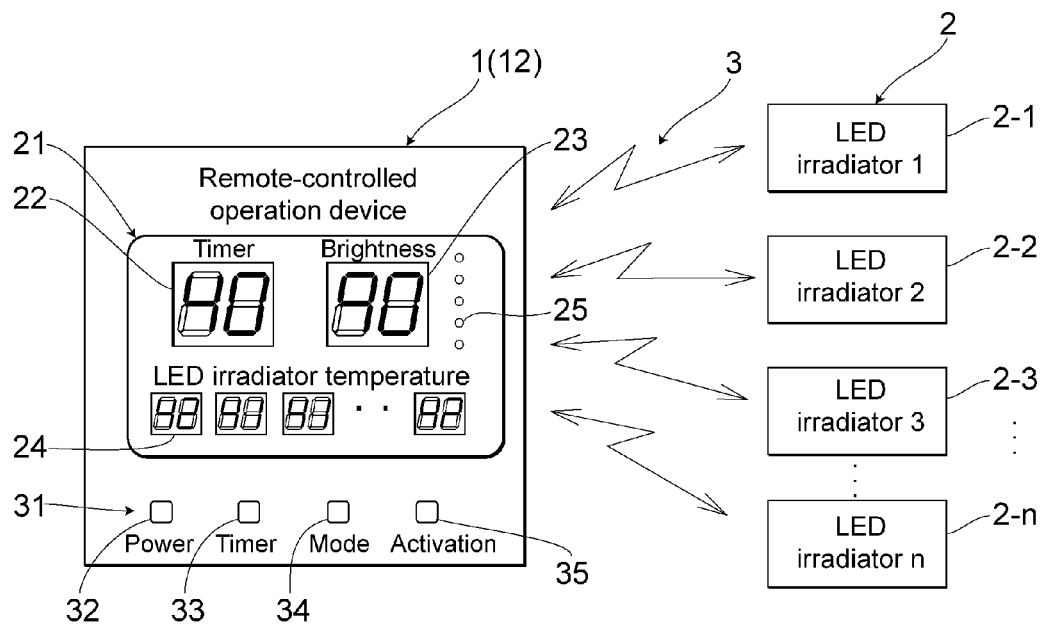
FIG. 2 is a diagram showing an exterior structure of a wireless living body stimulator of a preferred embodiment of the invention, the wireless living body stimulator being operated through bidirectional wireless remote control.

In the beginning, an exterior structure of the stimulator is described with reference to FIG. 1 and FIG. 2. As shown in both of these drawings, a numerical symbol "1" represents an operation device; a numerical symbol "2" represents one or more movable LED irradiators as light irradiators; and a numerical symbol "3" represents one or more communication tools for electrically connecting the operation device 1 to each LED irradiator 2. Here, as shown in FIG. 1 and FIG. 2, "n" sets of LED irradiators 2-1 to 2-n are connected to the one set of operation device 1. However, no limitation shall be imposed on the number of the LED irradiators 2 used. That is, n is a natural number.

FIG. 1 shows a wire controlled living body stimulator. Particularly, each of the communication tools 3 is a wire such as a flexible cable, and the operation device 1 is provided as a main unit operation device 11 used to directly operate each LED irradiator 2. In contrast, FIG. 2 shows a living body stimulator operated through bidirectional wireless remote control. Particularly, each communication tool 3 is now wireless, and the operation device 1 is provided as a remote-control operation device 12 used to remotely operate each LED irradiator 2. Therefore, a transceiver (no shown) enabling a wireless communication through the communication tool(s) 3 is individually installed in the remote-control operation device 12 and each LED irradiator 2 shown in FIG. 2. The main unit operation device 11 and the remote-control operation device 12 share a nearly identical exterior structure with each other.

A display section 21 and an operation section 31 are located on the front surface of the operation device 1. Main composition elements of the display section 21 include a timer display 22, a brightness display 23 and at least one LED irradiator temperature display 24 that are each made of seven-segment LED displays. Other main composition elements of the display section 21 include an operating state display 25 established by aligning a plurality of LED lamps. Here, the operation section 31 is provided below the display section 21; and main composition elements of such operation section 31 include a power switch 32, a timer switch 33, a mode-changing switch 34 and an activation switch 35 that are each installed as a push button. In fact, the display section 21 may employ various kinds of displays other than LED displays. Similarly, the operation section 31 may also employ various kinds of operating parts other than push buttons.

Figure 3:
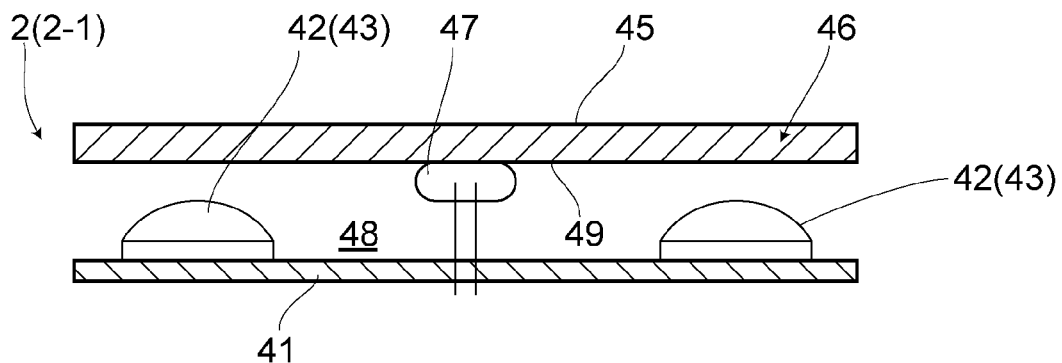
FIG. 3 is a vertical cross-sectional view of a main part of a preferred LED irradiator of the aforementioned embodiment, this LED irradiator serving as both a light source and a preheating unit.

FIG. 3 is a vertical cross-sectional view of a main portion of a preferred LED irradiator 2. Here, although only the first LED irradiator 2-1 is shown as a typical example, other LED irradiators 2-2 to 2-n each have a structure identical to that of the first LED irradiator 2-1. In FIG. 3, a numerical symbol "41" represents a wiring substrate obtained by performing pattern formation on the surface of a plate-shaped insulator, using a fine metal conductor; and a numerical symbol "42" represents one or more LEDs attached to appropriate locations on the wiring substrate 41. As shown in FIG. 3, a plurality of the LEDs 42 installed inside the LED irradiator 2 serve as a light source 43 for irradiating a living body.

Provided in an irradiation direction of each LED 42 is a light transmissive panel 46 having an irradiation surface 45 that is exposed on the outside of the LED irradiator 2. This light transmissive panel 46 is attached to an outer frame member (not shown) of the LED irradiator 2. The irradiation surface 45 serves as a living-body contact surface that comes into contact with the bare skin of the living body. That is, the lights emitted from each LED 42 when using the stimulator will pass through the light transmissive panel 46, and then irradiate the living body that is in contact with the irradiation surface 45.

Other than the LEDs 42, also attached to the wiring substrate 41 is a temperature sensor 47 as a temperature detection unit for detecting the temperature of the irradiation surface 45. Specifically, this temperature sensor 47 and the LEDs 42 are disposed in an inner space 48 of the LED irradiator 2 that is formed between the wiring substrate 41 and the light transmissive panel 46. More specifically, a thermosensitive part of the temperature sensor 47 abuts against an inner surface 49 opposite to the irradiation surface 45 of the light transmissive panel 46. That is, the light transmissive panel 46 of the present embodiment not only has a light transmissive property, but is made of a material with a thermal conductivity higher than that of the outer frame member of each LED irradiator 2 such that the temperature sensor 47 can quickly detect a change in the temperature of the irradiation surface 45.

Here, no limitation is imposed on the emission wavelength of each LED 42 used in this embodiment. That is, other than LEDs 42 only emitting a red light or LEDs 42 only emitting a light other than a red light, it is possible to combine together LEDs 42 individually emitting a blue light, a red light and a green light such that a full-color configuration can be established. Moreover, a pseudo white color can also be created by combining a LED(s) 42 emitting a blue light and a fluorescent body. Furthermore, the light source 43 shall not be limited to the LEDs 42 as long as the light source 43 used is capable of irradiating lights of various wavelengths including an infrared light and an ultraviolet light. However, in this embodiment, since the main purpose is to control the heat generated from each LED irradiator 2 (i.e. output control), it is required that the light source 43 be a so-called heat generating light source capable of generating heat whose amount of heat generation is obtained by multiplying an output thereof by a given coefficient.

Figure 4:
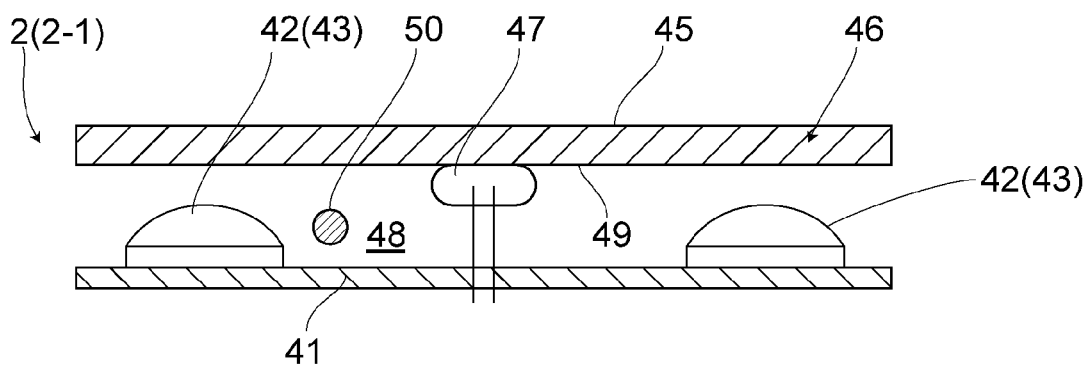
FIG. 4 is a vertical cross-sectional view of a main part of a preferred LED irradiator of the aforementioned embodiment, this LED irradiator being equipped with a heat generating unit solely serving as a preheating unit.

The light source 43 shown in FIG. 3 also serves as a preheater for preheating the irradiation surface 45 to a temperature (e.g. about 35° C. to 37° C.) that induces no cold feeling. Particularly, such preheating of the irradiation surface 45 takes place as the light source 43 emits light and thus generates heat before starting to use the living body stimulator. In this case, in order to prevent a user from being affected by a light leaking from each LED irradiator 2 at the time of preheating, it is preferred that at least the entire irradiation surface 45 of such LED irradiator 2 be covered by a housing device (not shown) such as a charging stand when the LED irradiator 2 is stored in this housing device. However, other than the light source 43, there may also be installed a heat generating unit 50 exclusively for performing preheating. FIG. 4 is a vertical cross-sectional view of a main portion of such a kind of LED irradiator 2 with the heat generating unit 50 installed therein. In FIG. 4, other than the fact that the heat generating unit 50 is now added, the LED irradiator 2 shown therein shares an identical structure with the LED irradiator 2 shown in FIG. 3.

The heat generating unit 50 is made of, for example, an electric heating element; and is provided in the inner space 48 of the LED irradiator 2 in such a way that it is installed above the wiring substrate 41 or in the vicinity of the light transmissive panel 46. When performing preheating, the heat generating unit 50 is electrically conducted as a result of switching from the light source 43. That is, the light can be prevented from leaking from the LED irradiator 2 by stopping the light emission of the light source 43 in the first place. Instead, by successively switching to and from the light source 43 and the heat generating unit 50 such that the two are alternately conducted or not conducted, the flashing light source 43 can also clearly show the user that preheating is taking place.

Figure 5:
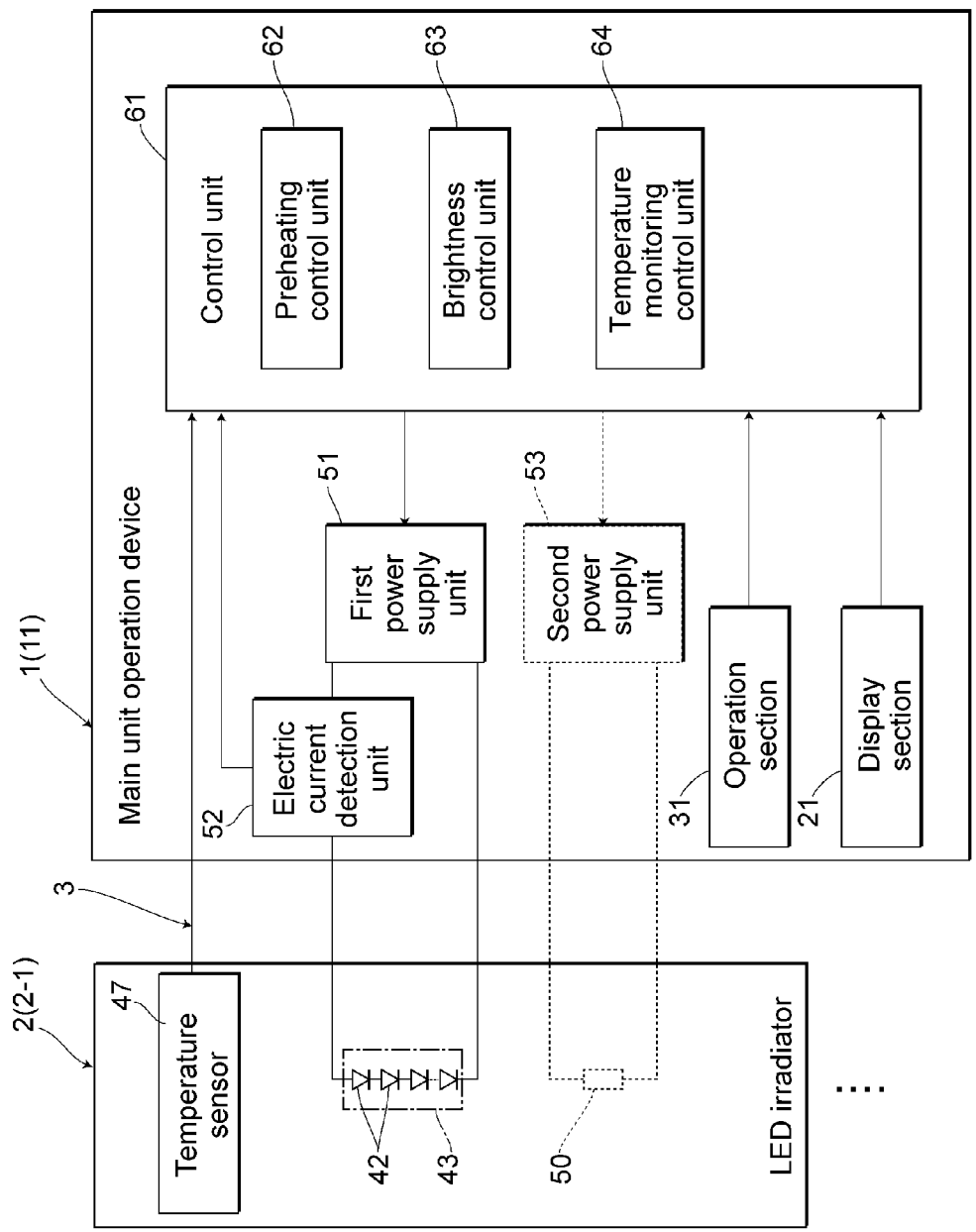
FIG. 5 is a diagram showing an electrical configuration of the wired living body stimulator of the aforementioned embodiment.

FIG. 5 is a diagram showing an electrical configuration of the aforementioned wire controlled living body stimulator. As for the LED irradiator(s) 2, only the configuration of the first LED irradiator 2-1 is shown in FIG. 5. In fact, other LED irradiators 2-2 to 2-*n* share an identical configuration with the first LED irradiator 2-1.

The light source 43 installed in each LED irradiator 2 is configured in a manner such that the plurality of the LEDs 42 are connected to one another in series. Further, the temperature sensor 47 is individually installed in each LED irradiator 2. This is because, as shown in FIG. 5, the LEDs 42 arranged in the LED irradiator 2 are not individually controlled, but are all connected to one another in series. In FIG. 5, the heat generating unit 50 and a circuit configuration thereof are shown in dashed lines; this indicates that the heat generating unit 50 is not required for the LED irradiator 2 having the configuration shown in FIG. 3.

Meanwhile, the main unit operation device 11 internally includes: a first power supply unit 51 for supplying a first power to the series circuit of the plurality of the LEDs 42 as the light source 43; an electric current detection unit 52 for detecting the amount of the electric current flowing through the aforementioned series circuit; and a second power supply unit 53 for supplying a second power to the heat generating unit 50.

Though not shown in the drawings, the first power supply unit 51 is composed of a boosting circuit for applying to the series circuit of the plurality of the LEDs 42 a DC voltage (e.g. 3.7 V to 24 V) obtained by boosting an input voltage; and an electric current regulator for regulating the electric current flowing through the aforementioned series circuit, in accordance with an on/off time of a PWM (Pulse Width Modulation) control signal supplied from a later described control unit 61. However, instead of an electric current regulator as a light control unit capable of controlling the brightness of the LEDs 42, there may be employed a voltage regulator capable of changing and thus regulating the voltage applied to the series circuit of the plurality of the LEDs 42, in accordance with the on/off time of the PWM control signal. In each case, the brightness of the light source 43 can be varied and regulated in accordance with a duty ratio of the PWM control signal. The booster is configured in a way such that it can supply a DC voltage sufficient to light up the multiple LEDs 42 that are connected in series.

The second power supply unit 53 includes, for example, a switching unit (not shown) turning on or off the power supply to the heat generating unit 50 upon receiving a conduction/non-conduction control signal from the control unit 61. The aforementioned configurations of the first power supply unit 51 and the second power supply 53 are merely an example(s) thereof. In fact, there may be employed another configuration as long as the power consumption of each of the light source 43 and the heat generating unit 50 can be individually varied and regulated.

The control unit 61 is installed inside the main unit operation device 11. Particularly, the control unit 61 fetches detection outputs from the temperature sensor 47 and the electric current detection unit 52, upon receiving various instruction signals from the operation section 31 as the user operates the switches. In this way, at given timings determined by an internally installed timer unit, the control unit 61 is capable of outputting a first control signal such as the PWM control signal to the first power supply unit 51 such that the power consumption of each LED 42 i.e. the light source 43 can be controlled; outputting a second control signal such as the conduction/non-conduction control signal to the second power supply unit 53 such that the power consumption of the heat generating unit 50 can be controlled; and outputting a display control signal to the display section 21 such that the display mode of the display section 21 can be controlled. Though not shown in the drawings, other than the timer unit, this control unit 61 also includes, for example, a control processor such as a central processing unit (CPU), a storage unit and an input-output unit.

As a software configuration that functions by reading a program(s) from the storage unit, the control unit 61 further includes a preheating control unit 62, a brightness control unit 63 and a temperature monitoring control unit 64.

The preheating control unit 62 is configured as follows. That is, the preheating control unit 62 allows the irradiation surface 45 to be preheated by electrically conducting the light source 43 and heat generating unit 50 as preheating units in a way such that the temperature of the irradiation surface 45 may get higher than the air temperature and then become closer to the body temperature from the moment when the power switch 32 is pushed with the main unit operation device 11 being in an off state to the moment when the activation switch 35 is pushed to order the beginning of use of the device. Particularly, the preheating control unit 62 is also configured in the following manner. That is, after pushing the power switch 32, the irradiation surface 45 is preheated as the light source 43 and heat generating unit 50 are electrically conducted for a given period of time. During this period of time, when the preheating control unit 62 has determined, based on the detection output from the temperature sensor 47, that the temperature of the irradiation surface 45 has reached a preset temperature (e.g. 37° C.) close to the body temperature, the electric conduction of the light source 43 and heat generating unit 50 will stop such that the irradiation surface 45 can stop being preheated any further. In contrast, if it is determined that the temperature of the irradiation surface 45 has not yet reached 37° C., the electric conduction of the light source 43 and heat generating unit 50 will continue until the given period of time elapses, thus completing preheating.

Here, it is preferred that the given period of time be set in such a manner that while it is preset by the preheating control unit 62 by the time of shipping the device from the factory, the user can actually change such given period of time by operating the operation section 31 of the main unit operation device 11 at any time later. For example, the given period of time i.e. preheating period can be set to "3 min," "5 min" or "10 min" such that the preheating control unit 62 can, in a controlled manner, allow the light source 43 and heat generating unit 50 to be electrically conducted during such preheating period. In this case, preheating shall not take place again by electrically conducting the light source 43 and heat generating unit 50, after the preheating time has elapsed since the power switch 32 was switched on.

Moreover, the preheating control unit 62 may also be configured in a way such that other than the first setting where preheating shall not take place again after the period of "3 min," "5 min" or "10 min," there can also be performed a second setting where preheating takes place again in, for example, a "continuous manner." Specifically, as a result of performing the second setting by operating the operation section 31, the electric conduction of the light source 43 and heat generating unit 50 will be turned off when the temperature of the irradiation surface 45 has increased to 37° C. as a second temperature. There, when the temperature of the irradiation surface 45 has then decreased to 35° C. as a third temperature, the electric conduction of the light source 43 and heat generating unit 50 will be turned on such that the irradiation surface 45 is allowed to be preheated again in a repetitive manner. The purpose of enabling such second setting is to maintain the temperature of the irradiation surface 45 at a temperature close to the body temperature even after a long period of time has elapsed from pushing the power switch 32 to the irradiation surface 45's coming into contact with the bare skin of the living body.

The brightness control unit 63 is configured as follows. That is, after the activation switch 35 has been pushed, the brightness control unit 63 operates subsequently after the operation of preheating control unit 62. Particularly, the brightness control unit 63 fetches the detection output from the temperature sensor 47 to send to the first power supply unit 51 a PWM control signal of a duty ratio causing the temperature of the irradiation surface 45 to become not higher than 42° C., thus controlling the brightness of each LED 42 composing the light source 43.

In addition, the brightness control unit 63 of this embodiment is configured in a way such that, each time the mode-changing switch 34 is pushed, there can be selectively set a first mode enabling a constant power consumption for the irradiation; or a second mode realizing a constant irradiation period. When the first mode has been selected, the brightness control unit 63 will pick up the detection output from the electric current detection unit 52 every given period of time, thereby making it possible to calculate an integrated power for the irradiation by monitoring the electric current of the light source 43. The brightness control unit 63 then keeps sending out the PWM control signal until such integrated power for the irradiation has become a predetermined irradiation power, thus lighting up the light source 43 at a given brightness. Therefore, in the process of lighting up the light source 43, when the electric current flowing through the light source 43 has been decreased from a prescribed value to another value by changing the duty ratio of the PWM control signal such that the temperature of the irradiation surface 45 will not exceed 42° C., it takes an excessive period of time for the internally calculated integrated power for the irradiation to reach the predetermined irradiation power. Here, it is considered that the brightness control unit 63 has the following configuration. That is, since there is a definite relationship between the current flowing through the light source 43 i.e. the power consumption of the light source; and the brightness of the light source 43 as an output thereof, when the brightness control unit 63 has operated to decrease the brightness of the light source 43 from a first value to a second value upon receiving the detection output from the temperature sensor 47, the irradiation period of the light source 43 will be extended in accordance with the difference between the first value and the second value.

However, when the second mode has been selected, the brightness control unit 63 will operate to make the irradiation period of the light source 43 constant even after decreasing the electric current flowing through the light source 43 from the prescribed value to an other value. This irradiation period can be optionally changed and set by operating the operation section 31. In this embodiment, the irradiation period can be changed and set in a range of 5 min to 30 min at five minute intervals, each time the timer switch 33 is pushed. Further, when the activation switch 35 as a starting switch has been pushed, the brightness control unit 63 will send out the PWM control signal to light up the light source 43; and initiate a subtraction process with respect to the irradiation period selected, using the aforementioned timer unit. This subtraction process allows the remaining time to be shown on the timer display 22. That is, when the irradiation period has been reached according to the timer unit, the PWM control signal will stop being sent out for the purpose of turning off the light source 43, thus achieving a constant irradiation period of the light source 43. However, when the activation switch 35 has been pushed during the subtraction process, the subtraction process will stop temporarily; and the light source 43 will be turned off as well. Later, when the activation switch 35 has again been pushed, the subtraction process will restart; and the light source 43 will again be turned on.

In short, other than the first mode, the brightness control unit 63 also allows the second mode to be selected. The purpose of such configuration is to avoid a prolonged treatment of the first mode for which some users dislike. Further, as for the first mode, there exists a problem where each of the multiple LED irradiators 2-1 to 2-$n$ used finishes irradiating in mismatched timing. In order to solve this problem, there may also be made available yet a third mode which is a finish-time matching mode allowing all the LED irradiators 2-1 to 2-$n$ to finish irradiating at an identical time. For example, the LED irradiator 2-1 whose irradiation surface 45 has first reached the temperature of 42° C. may be used as a reference, and the times of the other LED irradiators 2-2 to 2-$n$ are then matched to an extended time (electric current) of such LED irradiator 2-1.

In this embodiment, other than the first mode to the third mode, various modes such as a "continuous mode" and an "intermittent irradiation mode" can be set at the operation section 31. For example, as for the intermittent irradiation mode allowing the light source 43 to intermittently perform light irradiation every given period of time, preset are the rising and falling traits of the illuminance (brightness); and the intervals thereof. Further, this embodiment is configured such that the mode selected successively changes each time the mode-changing switch 34 of the operation section 31 is pushed.

The temperature monitoring control unit 64 is configured as follows. That is, after pushing the power switch 32, the temperature monitoring control unit 64 picks up, every given period of time, the detection output from the temperature sensor 47 installed in each of the LED irradiators 2-1 to 2-$n$, thereby making it possible to constantly monitor the temperatures of the irradiation surfaces 45 of the LED irradiators 2-1 to 2-$n$, and then output to the display section 21 a monitoring result as the display control signal. Upon receiving such display control signal, the LED irradiator temperature display(s) 24 of the display section 21 will individually show the temperatures of the irradiation surfaces 45 of the LED irradiators 2-1 to 2-$n$. Further, the monitoring result of the temperature monitoring control unit 64 may also be outputted as, for example, a voice signal. That is, an output of any kind is acceptable as long as the user is capable of recognizing the current temperature of each irradiation surface 45.

Other than the temperature of each irradiation surface 45, the temperature monitoring control unit 64 of this embodiment is also capable of constantly monitoring the brightness of the light source 43 of each of the LED irradiators 2-1 to 2-$n$; and outputting a monitoring result thereof to the display section 21 as the display control signal. This is because the temperature monitoring control unit 64 also picks up, every given period of time, the detection output from the electric current detection unit 52 installed in each of the LED irradiators 2-1 to 2-$n$. Thus, the brightness of the light source 43 of each of the LED irradiators 2-1 to 2-$n$ can be shown, in a switchable manner, on the brightness display 23 of the display section 21.

As for the wired living body stimulator shown in FIG. 2, since a required operating voltage is supplied from the main unit operation device 1 to each section of each of the LED irradiators 2 through the communication tool(s) 3, no power-supply unit needs to be installed in the LED irradiator(s) 2. However, as for the living body stimulator operated through bidirectional wireless remote control, since power supply through the communication tool(s) 3 is limited, it is preferred that a power-supply unit capable of performing charging and discharging be installed in the LED irradiator(s) 2, and that the operating voltage be supplied to each section of each of the LED irradiators 2. In this case, when the LED irradiator(s) 2 are stored in the charging stand, a power for charging is capable of being supplied to the power-supply unit through the charging stand. Further, as shown in FIG. 5, since the first power supply unit 51, the electric current detection unit 52 and the second power supply unit 53 are not disposed on the side of the operation device 1, but on the side of the LED irradiator(s) 2, communication through the communication tool(s) 3 only requires a small amount of electric power. This type of configuration can also be applied to the wired living body stimulator.

Figure 6:
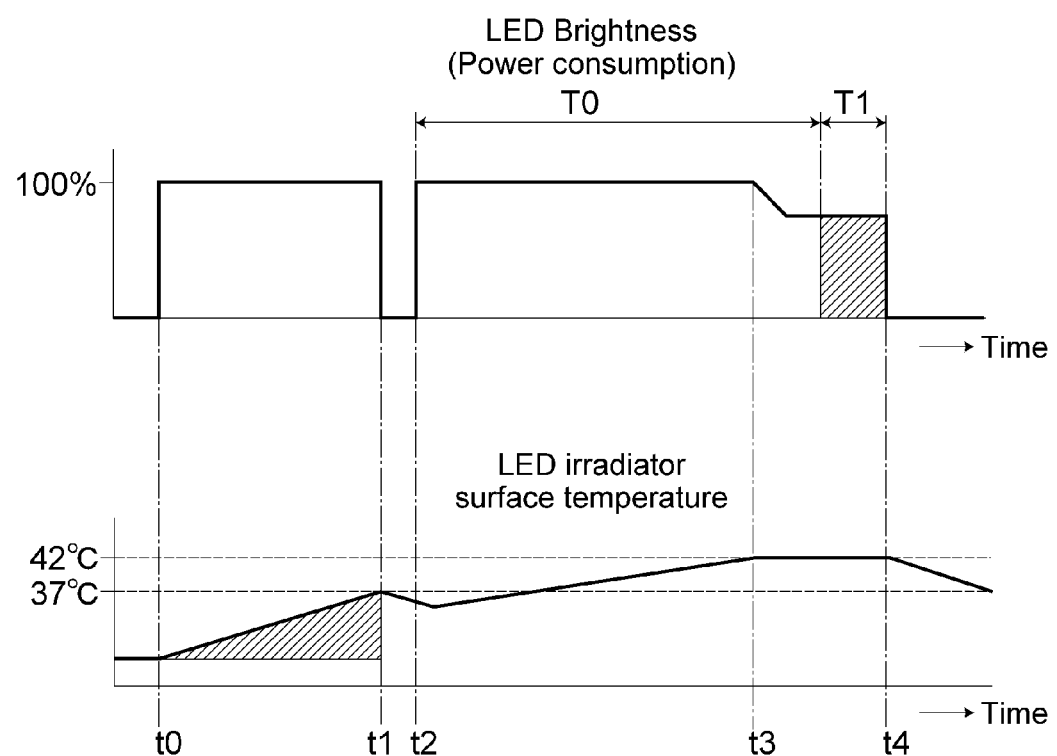
FIG. 6 is a graph showing a brightness variation of an LED (shown in the upper part) and the irradiation surface temperature thereof (shown in the lower part) over time after operating a power switch.

The functions of the aforementioned configurations are described hereunder with reference to the graphs shown in FIG. 6 to FIG. 8. As for each of these graphs, the upper section titled "LED brightness (power consumption)" shows a change in the brightness i.e. power consumption of each LED 42 with respect to time, with a predetermined level being expressed as 100%. Further, the lower section titled "LED irradiator surface temperature" shows a change in the temperature of the irradiation surface 45 of the LED irradiator 2. Although mainly described hereunder is the operation of the wired living body stimulator, the operation of the living body stimulator operated through bidirectional wireless remote control is basically identical to that of the wired living body stimulator except that its communication method using the communication tool(s) 3 differs from that of the wired living body stimulator.

FIG. 6 is a graph showing changes in the brightness of the LED 42 and the temperature of the irradiation surface 45 with time, after pushing the power switch 32 from the off state where no power-supply voltage is yet supplied to the main unit operation device 11. As shown in this graph, when the power switch 32 has been pushed at a time t0, a power-supply voltage will be supplied to the main unit operation device 11 such that a given operating voltage will then be supplied to the control unit 61 and so on. Upon receiving such operating voltage, the preheating control unit 62 of the control unit 61 will output the PWM control signal to the first power supply unit 51 to light up each LED 42 of the light source 43 and start preheating the irradiation surface 45 using a heat thus generated, thereby making it possible to warm the irradiation surface 45 to a temperature close to the body temperature.

The preheating period is set in the preheating control unit 62. That is, the preheating control unit 62 determines whether or not the temperature of the irradiation surface 45 has increased to 37° C. as a preset temperature close to the body temperature, during the period between the start of preheating and the end of the preheating period. Here, the temperature of the irradiation surface 45 is obtained through the detection output from the temperature sensor 47. Particularly, when it has been determined that the temperature of the irradiation surface 45 has reached 37° C. at a time t1, the preheating control unit 62 will stop sending the PWM control signal to the first power supply unit 51 to turn off each LED 42 and thus finish preheating the irradiation surface 45. The temperature of the irradiation surface 45 will moderately decrease thereafter. However, since the irradiation surface 45 will maintain a temperature close to the body temperature for a certain period of time, there can still be resolved an uncomfortable feeling induced by the difference between the body temperature and the temperature of the irradiation surface 45 at the time of wearing the device, even when the bare skin of the living body has come into contact with the irradiation surface 45 as a result of moving the LED irradiator 2 for its intended use.

Here, when, for example, the ambient temperature is significantly low due to the surrounding environment, preheating may end without the irradiation surface 45 reaching the temperature of 37° C. even at the end of the preset preheating period. In order to deal with such a kind of circumstance, this embodiment allows the preheating period to be changed, thus making it possible to preheat the irradiation surface 45 to a temperature close to the body temperature regardless of the change in the surrounding environment. Further, after the preset preheating period has elapsed, preheating will not be performed again regardless of the temperature of the irradiation surface 45. However, if the preheating control unit 62 is configured in a manner such that preheating takes place again as the LEDs 42 are again lighted up when the temperature of the irradiation surface 45 has decreased to 35° C. before pushing the activation switch 35 next time, the uncomfortable feeling due to the difference between the body temperature and the temperature of the device at the time of wearing the same can be reliably resolved regardless of when the bare skin of the living body will come into contact with the irradiation surface 45 after preheating was started.

Further, as a preheating unit for preheating the irradiation surface 45, there may also be used the heat generating unit 50 instead of the LEDs 42. In such case, the preheating control unit 62 does not send the PWM control signal to the first power supply unit 51, but sends the conduction/non-conduction control signal to the second power supply unit 53. That is, the LEDs 42 are not lighted up at the time of performing preheating. Instead, the heat from the electrically conducted heat generating unit 50 is used to heat the irradiation surface 45 to a temperature close to the body temperature. Therefore, the lights leaking from the LEDs 42 can be prevented from affecting the user without having to store the LED irradiator(s) 2 in the housing device.

As yet another example, switching may take place between the LEDs 42 and the heat generating unit 50 in a successive manner such that the LEDs 42 and the heat generating unit 50 are alternately electrically conducted or not conducted. Particularly, there may also exist a period when both the LEDs 42 and the heat generating unit 50 are electrically conducted at the time of switching. Here, the flash of the LEDs 42 can easily indicate to the user that preheating is taking place. Further, by utilizing both the LEDs 42 and the heat generating unit 50, there can also be achieved an effect of obtaining from both the LEDs 42 and the heat generating unit 50 the heat sufficient to rapidly warm the irradiation surface 45.

In this way, either before or after allowing the living body to come into contact with the irradiation surface 45, when the activation switch 35 has been pushed at a time t2 to order the beginning of use of the device, the brightness control unit 63 as an alternative to the preheating control unit 62 will output the PWM control signal to the first power supply unit 51 to light up the LEDs 42 composing the light source 43 and thus start treating the living body through the light irradiation from the light source 43. The brightness of the LEDs 42 at that time is the preset first value.

During the period when light is being irradiated from the light source 43, the brightness control unit 63 serves to control the brightness of the LEDs 42 such that the temperature of the irradiation surface 45 that is detected via the detection output from the temperature sensor 47 does not exceed 42° C. which is lower than 44° C. as a temperature causing low temperature burn. As shown in the example of FIG. 6, when the temperature of the irradiation surface 45 has reached 42° C. at a time t3, the duty ratio of the PWM control signal to be sent to the first power supply unit 51 will be changed such that the temperature of the irradiation surface 45 will not increase any further. Thus, the brightness of the LEDs 42 is allowed to decrease from the first value so far to the preset second value as an other value; and the temperature of the irradiation surface 45 is controlled to 42° C.

With the first mode enabling a constant power consumption for the irradiation being set, the brightness control unit 63 picks up, every given period of time, the detection output from the electric current detection unit 52, thereby making it possible to calculate the integrated power for the irradiation as a cumulative amount of the power consumption based on the amount of the electric current of the LEDs 42 that is obtained from the detection output of the electric current detection unit 52. Moreover, the PWM control signal will be continuously sent to the first power supply unit 51 until the integrated power for the irradiation has become the predetermined irradiation power consumption. Then, when the integrated power for the irradiation has reached the predetermined irradiation power consumption at a time t4, the PWM control signal will stop being sent to the first power supply unit 51, thus ending the treatment via the light irradiation from the light source 43.

That is, in the first mode, the irradiation period of the LEDs 42 is regulated to obtain a constant cumulative amount of the irradiation power from the light source 43, while controlling the brightness of the LEDs 42 such that the temperature of the irradiation surface 45 does not exceed 42° C. In this way, without increasing the temperature of the irradiation surface 45 more than necessary, the living body in contact with the irradiation surface 45 can be protected; and there can be obtained a stable treatment effect of the light stimulus from the light source 43. As shown in the example of FIG. 6, as compared to a treatment period T0 for which irradiation is performed with the brightness of the LEDs 42 being maintained at the first value, a treatment period where the brightness of the LEDs 42 eventually decreases from the first value to the second value is extended by a time T1. Particularly, the larger the difference between the first value and the second value is, the longer this extended time T1 becomes.

For comparison between this embodiment and a conventional device, FIG. 7 and FIG. 8 show changes in the temperature of the irradiation surface 45 with time; and changes in the brightness of the LEDs 42 with time, after operating the activation switch 35. As mentioned above, the brightness control unit 63 of this embodiment serves to regulate the irradiation period of the LEDs 42 to obtain a constant cumulative amount of the irradiation power from the light source 43, while controlling the brightness of the LEDs 42 such that the temperature of the irradiation surface 45 does not exceed 42° C. In contrast, as for the conventional device, the irradiation period of the LEDs 42 is constant (from a time t2 to a time t4 shown in FIG. 8). Particularly, the brightness of the LEDs 42 does not decrease during such period, even when the temperature of the irradiation surface 45 has exceeded 42° C. Therefore, during a period Tx shown in FIG. 8, there is continuously exhibited an overtemperature state (state of excessively elevated temperature) where the temperature of the irradiation surface 45 in contact with the living body is greater than 42° C.

Although not shown in FIG. 6 and FIG. 7, the brightness control unit 63 of this embodiment also allows there to be set the second mode realizing a constant irradiation period, instead of the first mode. In the second mode, the living body in contact with the irradiation surface 45 is likewise protected by controlling the brightness of the LEDs 42 such that the temperature of the irradiation surface 45 does not exceed 42° C. However, the second mode allows the user to selectively change and set the irradiation period within the range of 5 min to 30 min by operating the timer switch 33. Thus, avoided is the user's dislike for a prolonged treatment period when only the first mode is available; and the living body can be irradiated with light for the preferred duration of treatment period set.

Further, when using the multiple LED irradiators 2-1 to 2-n, it is desirable that the brightness control unit 63 in the first mode has a function capable of matching the irradiation ending times of the LED irradiators 2-2 to 2-n to that of, for example, the LED irradiator 2-1 which is the first LED irradiator whose irradiation surface 45 has first reached the temperature of 42° C. With this function of the brightness control unit 63, even when a variation(s) are observed in the LED irradiators 2-1 to 2-n, all the LED irradiators 2-1 to 2-n are allowed to finish irradiation from the light source 43 at an identical time.

The aforementioned sequence of operations following pushing the power switch 32, allows the temperature monitoring control unit 64 to fetch, every given period of time, the detection output from the temperature sensor 47 installed in each of the LED irradiators 2-1 to 2-n, thus making it possible to constantly monitor the current temperatures of their irradiation surfaces 45 of all the LED irradiators 2-1 to 2-n. Here, the current temperatures of such irradiation surfaces 45 are fetched from the detection outputs of the temperature sensor 47. The monitoring result is then outputted as the display control signal from the temperature monitoring control unit 64 to the display section 21 such that the temperatures of the irradiation surfaces 45 of the LED irradiators 2-1 to 2-n can be individually displayed on the LED irradiator temperature display(s) 24. That is, since the current temperature of each irradiation surface 45, as a treatment temperature, can be constantly monitored on the side of the main unit operation device 11, it is possible to prepare for situations where the device is not being properly controlled (e.g. malfunctions and failures).

Moreover, when the temperature monitoring control unit 64 has determined that the temperature of a certain irradiation surface 45 has become uncontrollably abnormal, the temperature monitoring control unit 64 will then send an alarm signal to the particular abnormal LED irradiator e.g. LED irradiator 2-1 while maintaining the communication with the main unit operation device 11, but shutting down other circuits (e.g. the boosting unit and the electric current regulator that compose the first power supply unit 51). For example, by outputting such alarm signal to the display section 21, the operating state display 25 can display the state of alarm. Alternatively, this alarm signal may also be outputted to a sounding unit such as a buzzer to inform the alarming state. In each case, the user is capable of recognizing the abnormal state of the device; and the electric current supply to the abnormal LED irradiator 2-1 can be stopped immediately such that safety is improved.

In this way, the living body stimulator of this embodiment serves to stimulate a living body through the light irradiation from the light source 43. Particularly, the living body stimulator of this embodiment includes the temperature sensor 47 and the brightness control unit 63. More particularly, the temperature sensor 47 serves as a temperature detection unit for detecting the temperature of the irradiation surface 45 in contact with the living body. Further, the brightness control unit 63 picks up the detection output from the temperature sensor 47 to change and control the brightness of the light source 43 in a manner such that the temperature of the irradiation surface 45 becomes not higher than 42° C. Furthermore, when the control unit has been regulated to decrease the brightness of the light source from the first value to the second value, the brightness control unit 63 will extend the period of irradiation from the light source 43 in accordance with the difference between the first value and the second value i.e. a decrease in brightness.

Here, the brightness control unit 63 serves to automatically control the brightness of the light source 43 such that the temperature of the irradiation surface 45 in contact with the living body does not exceed 42° C. which is lower than 44° C. as the temperature causing low temperature burn. In addition, when the brightness of the light source 43 has been decreased from the first value to the second value through control, the time of irradiation from the light source 43 to the living body will be automatically extended such that the brightness decreased will be compensated, thus preventing the treatment effects from varying. Therefore, there can be achieved a stable treatment effect of the light stimulus from the light source 43, without increasing the temperature of the irradiation surface 45 more than necessary.

Other than the temperature sensor 47, the living body stimulator of this embodiment also includes one or multiple LED irradiators 2 as light irradiators for irradiating lights from the light source 43 through the irradiation surfaces 45; and the operation device 1 electrically connected to the LED irradiator(s) 2 in a wired or wireless fashion. Further, the control unit 61 of the operation device 1 includes the temperature monitoring control unit 64 capable of constantly monitoring the temperature of the irradiation surface 45 of each LED irradiator 2 by receiving the detection output from the temperature sensor 47. Furthermore, this temperature monitoring control unit 64 serves to output the monitoring result thus obtained to, for example, the display section 21.

In this case, on the side of the operation device 1 that is electrically connected to the LED irradiator(s) 2, outputted from the temperature monitoring control unit 64 is the result obtained by constantly monitoring the temperature of each irradiation surface 45 during the use of the device, such result being signaled to the user in the form of, for example, a display or a sound. Thus, even when the temperature of each irradiation surface 45 cannot be properly controlled due to a malfunction or failure of the device, the user is capable of recognizing the abnormal heat generation through the output of the temperature monitoring control unit 64.

Further in this embodiment, the living body stimulator includes the preheating control unit 62 to control the light source 43 and the heat generating unit 50 as preheating units such that the irradiation surface 45 of each LED irradiator 2 may be preheated before stimulating the living body through the light irradiation from the light source 43.

Specifically, the irradiation surface 45 is heated in advance by the light source 43 and/or the heat generating unit 50 to a temperature inducing no cold feeling, before irradiating the living body with light. Therefore, there can be resolved the uncomfortable feeling that occurs at the time of allowing the bare skin of the living body to come into contact with the irradiation surface 45.

Moreover, in this embodiment, the brightness control unit 63 is configured in a manner such that, by operating the mode-changing switch 34 as a mode switching unit, there can be selectively set either the first mode enabling a constant power consumption for the irradiation; or the second mode realizing a constant irradiation period. When the first mode is set, the period of irradiation from the light source 43 will be extended if the brightness of the light source 43 has decreased through regulation. Particularly, the time of irradiation from the light source 43 in this case will be extended in accordance with such decrease in the brightness of the light source 43. When the second mode is set, the light irradiation from the light source 43 will end in the preset irradiation period with the brightness of the light source 43 being controlled such that the temperature of the irradiation surface becomes not higher than 42° C.

Here, other than the first mode, there can also be set the second mode through the mode-changing switch 34. That is, both the first and second modes allow the living body in contact with the irradiation surface 45 to be protected while the treatment is being performed. Particularly, the second mode allows the user to avoid having the treatment period extended when only the first mode is available, thus resolving the user's dislike for a prolonged treatment period.

Further, in this embodiment, by operating the timer switch 33 as an irradiation period setting tool, the irradiation period of the second mode can be changed and set.

Therefore, with the second mode being set, the user is capable of irradiating the living body with light in a preset and preferred treatment period by operating the timer switch 33.

Also, the living body stimulator of this embodiment includes the multiple LED irradiators 2-1 to 2-n. Particularly, in the first mode, the brightness control unit 63 is configured in the manner such that the LED irradiator 2-1, for example, whose irradiation surface 45 has first reached the temperature of 42° C. may be used as a reference, and the irradiation ending times of the other LED irradiators 2-2 to 2-n are then matched to that of such LED irradiator 2-1.

In this case, even when a variation(s) are observed in the LED irradiators 2-1 to 2-n, all the LED irradiators 2-1 to 2-n are allowed to finish irradiation from the light source 43 at an identical time.

In addition, the temperature monitoring control unit 64 of this embodiment is configured as follows. That is, when the temperature monitoring control unit 64 has determined that the temperature of the irradiation surface 45 has become uncontrollably abnormal, it will stop power supply to a particular abnormal LED irradiator 2-1, for example; and send out the alarm signal, while maintaining the communication between such LED irradiator 2-1 and the main unit operation device 11 and keeping monitoring the temperature of the irradiation surface.

Thus, the user is capable of recognizing the abnormal state of the device; and the electric current supply to the abnormal LED irradiator 2-1 can be stopped immediately such that safety is improved.

Further, as for the preheating control unit 62 of this embodiment, the first setting is enabled as follows. That is, when the temperature of the irradiation surface 45 that is obtained from the detection output from the temperature sensor 47 has increased to, for example, 37° C. during the period between the start of preheating and the end of the preheating period, the light source 43 and the heat generating unit 50 as preheating units will stop being electrically conducted such that the preheating of the irradiation surface 45 will stop there. However, if the temperature of the irradiation surface 45 has not increased to 37° C. during such period, the light source 43 and the heat generating unit 50 will stop being electrically conducted at the moment when the preheating period elapses, thus finishing preheating the irradiation surface 45.

In this case, the first setting allows the light source 43 and the heat generating unit 50 to stop being electrically conducted when the irradiation surface 45 has reached the desired first temperature. Therefore, not only a wasteful power consumption can be avoided; but even when the temperature increase of the irradiation surface 45 is sluggish, the uncomfortable feeling occurring when the bare skin of the user's living body has come into contact with the irradiation surface 45 can be resolved as much as possible by keeping preheating the irradiation surface 45 until the preheating period elapses.

Further, in this embodiment, the preheating period can be changed and set by operating the operation section 31 as a preheating period setting unit.

Thus, by operating the operation section 31, the irradiation surface 45 can be preheated in a set and preferred preheating period after the user operates the power switch 32.

Further, as for the preheating control unit 62 of this embodiment, other than the first setting allowing no preheating to be performed again, the second setting is enabled as follows. That is, when the temperature of the irradiation surface 45 has increased to, for example, 37° C. as the second temperature, the electric conduction of the light source 43 and heat generating unit 50 will be turned off; but when the temperature of the irradiation surface 45 has decreased to, for example, 35° C. as the third temperature, the electric conduction of the light source 43 and heat generating unit 50 will be turned on.

In this case, the second setting allows the irradiation surface 45 to be repeatedly preheated in accordance with a change in the temperature of the irradiation surface 45. Particularly, even when a long period of time has elapsed from the moment when the power switch 32 was operated to the moment when the bare skin of the living body came into contact with irradiation surface 45, the irradiation surface 45 can be maintained at a temperature close to the body temperature, thus making it possible to reliably resolve the uncomfortable feeling that occurs when the bare skin of the user's living body has come into contact with the irradiation surface 45.

Although described above is an embodiment of the preset invention, this embodiment is merely presented as an example and thus shall not limit the scope of the invention. The embodiment presented can be carried in various other configurations. In short, such embodiment may be subjected to various kinds of omissions, displacements as well as modifications without departing from the scope of the invention. For example, there can also be employed a configuration allowing the first and second values in the above embodiment to be arbitrarily set and changed.

What is claimed:

1. A living body stimulator for stimulating a living body through a light irradiation from a light source, comprising:
   a temperature detection unit for detecting a temperature of an irradiation surface in contact with the living body; and
   a brightness control unit for variably controlling a brightness of said light source such that the temperature of said irradiation surface becomes not higher than 42° C., by receiving a detection output from said temperature detection unit, said brightness control unit extending an irradiation period of said light source in accordance with a decrease in the brightness of said light source when the brightness of said light source has been decreased through control,
   wherein said brightness control unit is configured to enable
   a setting of a first mode achieving a constant irradiation power consumption of said light source, said first mode extending the irradiation period of said light source in accordance with a decrease in brightness of said light source when the brightness of said light source has been decreased through control; and
   a setting of a second mode achieving a constant irradiation period of said light source, said second mode allowing a light irradiation from said light source to end in a preset irradiation period while controlling the temperature of said irradiation surface to not higher than 42° C.

2. The living body stimulator according to claim 1, further comprising:
   one or more light irradiators for irradiating lights from said light source through said irradiation surface; and
   an operation device electrically connected to said light irradiators in a wired or wireless manner, said operation device including a temperature monitoring control unit capable of constantly monitoring the temperature of said irradiation surface and outputting a monitoring result, by receiving the detection output from said temperature detection unit.

3. The living body stimulator according to claim 1, further comprising a preheating control unit allowing said irradiation surface to be preheated through control, before the living body is stimulated by the light irradiation from said light source.

4. The living body stimulator according to claim 1, further comprising an irradiation period setting tool for changing and setting the irradiation period in said second mode.

5. The living body stimulator according to claim 1, further comprising a plurality of light irradiators individually irradiating a light from said light source through said irradiation surface, wherein said brightness control unit, in said first mode, uses one of said light irradiators whose irradiation surface temperature has first reached 42° C. as a reference to match irradiation ending times of the rest of said light irradiators to an irradiation ending time of the light irradiator used as the reference.

6. The living body stimulator according to claim 2, wherein said temperature monitoring control unit, after determining that the temperature of said irradiation surface of a particular light irradiator has become abnormal, serves to stop power supply to said particular light irradiator and send out an alarm signal, while maintaining a communication between said particular light irradiator and said operation device and keeping monitoring the temperature of said irradiation surface.

7. The living body stimulator according to claim 3, further comprising a preheating unit for preheating said irradiation surface, wherein said preheating control unit enables a setting of a first mode in which, during a period between when preheating is started and when a preheating period elapses, power supply to said preheating unit is stopped to end preheating said irradiation surface when the temperature of said irradiation surface that is obtained through the detection output from said temperature detection unit has increased to a first temperature; or when the preheating period has elapsed if the temperature of said irradiation surface has not increased to the first temperature.

8. The living body stimulator according to claim 3, further comprising a preheating period setting unit for changing and setting a preheating period of said irradiation surface.

9. The living body stimulator according to claim 7, wherein said preheating control unit is configured to enable a setting of a second mode other than the first mode, the second mode allowing an electric conduction of said preheating unit to be turned off when the temperature of said irradiation surface has increased to a second temperature, but the electric conduction of said preheating unit to be turned on when the temperature of said irradiation surface has decreased to a third temperature.

10. The living body stimulator according to claim 2, further comprising a preheating control unit allowing said irradiation surface to be preheated through control, before the living body is stimulated by the light irradiation from said light source.

11. The living body stimulator according to claim 10, further comprising a preheating unit for preheating said irradiation surface, wherein said preheating control unit enables a setting of a first mode in which, during a period between when preheating is started and when a preheating period elapses, power supply to said preheating unit is stopped to end preheating said irradiation surface when the temperature of said irradiation surface that is obtained through the detection output from said temperature detection unit has increased to a first temperature; or when the preheating period has elapsed if the temperature of said irradiation surface has not increased to the first temperature.

12. The living body stimulator according to claim 10, further comprising a preheating period setting unit for changing and setting a preheating period of said irradiation surface.

13. The living body stimulator according to claim 11, wherein said preheating control unit is configured to enable a setting of a second mode other than the first mode, the second mode allowing an electric conduction of said preheating unit to be turned off when the temperature of said irradiation surface has increased to a second temperature, but the electric conduction of said preheating unit to be turned on when the temperature of said irradiation surface has decreased to a third temperature.

* * * * *